United States Patent [19]

Buchecker et al.

[11] Patent Number: 4,898,455

[45] Date of Patent: Feb. 6, 1990

[54] PYRIDINE LIQUID CRYSTALLINE COMPOUNDS

[75] Inventors: Richard Buchecker; Alfred Germann, both of Basel; Stephen Kelly, Kaiseraugst; Martin Schadt, Seltisberg, all of Switzerland

[73] Assignee: Hoffmann-La Roche Inc., Nutley, N.J.

[21] Appl. No.: 39,143

[22] Filed: Apr. 16, 1987

[30] Foreign Application Priority Data

Apr. 22, 1986 [CH]  Switzerland ............... 1638/86
Feb. 2, 1987 [CH]  Switzerland ............... 356/87

[51] Int. Cl.[4] .................. C09K 19/34; G02F 1/13; C07D 213/26
[52] U.S. Cl. .................. 350/350 R; 252/299.01; 252/299.5; 252/299.61; 350/350 S; 546/1; 546/290; 546/291; 546/292; 546/296; 546/300; 546/301; 546/302; 546/303; 546/326; 546/328; 546/329; 546/330; 546/331; 546/334; 546/335; 546/339; 546/342; 546/346; 546/350; 546/351
[58] Field of Search .............. 252/299.01, 299.61, 252/299.5; 250/350 R, 350 S; 546/1, 292, 291, 296, 300, 301, 302, 303, 290, 326, 328, 329, 330, 334, 335, 331, 339, 342, 346, 350, 351

[56] References Cited

U.S. PATENT DOCUMENTS

| | | | |
|---|---|---|---|
| 4,565,425 | 1/1986 | Petrzilka et al. | 252/299.61 |
| 4,621,901 | 11/1986 | Petrzilka et al. | 252/299.61 |
| 4,676,924 | 6/1987 | Dabrowski et al. | 252/299.61 |
| 4,684,220 | 8/1987 | Shionozaki et al. | 252/299.61 |
| 4,684,477 | 8/1987 | Sugimori et al. | 252/299.61 |
| 4,753,752 | 6/1988 | Raynes et al. | 252/299.61 |
| 4,765,924 | 8/1988 | Inoue et al. | 252/299.61 |
| 4,770,503 | 9/1988 | Buchecker et al. | 252/299.61 |
| 4,772,416 | 9/1988 | Goto et al. | 252/299.61 |
| 4,784,792 | 11/1988 | Inoue et al. | 252/299.61 |

FOREIGN PATENT DOCUMENTS

| | | | |
|---|---|---|---|
| 169327 | 1/1986 | European Pat. Off. | 252/299.61 |
| 0194153 | 9/1986 | European Pat. Off. | 252/299.61 |
| 0206228 | 12/1986 | European Pat. Off. | 252/299.61 |
| 206228 | 12/1986 | European Pat. Off. | 252/299.61 |
| 227004 | 7/1987 | European Pat. Off. | 252/299.61 |
| 3404055 | 10/1985 | Fed. Rep. of Germany | 252/299.61 |
| 3524489 | 1/1986 | Fed. Rep. of Germany | 252/299.61 |
| 3515373 | 11/1986 | Fed. Rep. of Germany | 252/299.61 |
| 3500909 | 7/1987 | Fed. Rep. of Germany | 252/299.61 |

(List continued on next page.)

OTHER PUBLICATIONS

Schadt, M., et al., International Display Research Conference, SID-IEEE, pp. 231-234, San Diego, Calif. (Oct. 15-17, 1985).

Pavluchenko, A. I. et al., Advances in Liq. Cryst. Res. and Appls., Ed. Bata, L., Pergamon Press, Oxford, pp. 1007-1013 (1980).
Karamysheva, L. A., et al., Mol. Cryst. Lir. Cryst., vol. 67, pp. 241-252 (1981).
Grachev, V. T. et al., Mol. Cryst. Liq. Cryst., vol. 65, pp. 133-144 (1981).
Grebyonkin, M. F., et al., Mol. Cryst. Liq. Cryst., vol. 129, pp. 245-257 (1985).
Nash, J. A., et al., Mol. Crystl. Liq. Cryst., vol. 25, pp. 299-321, (1974).
Seiko Epson KK, Derwent No. 86-235775/36, 1986.
Bofinger et al., Derwent No. 86-319979/49, 1986.
Krause et al., Derwent No. 86-299025/46, 1986.
Shionozak et al., Derwent No. 86-023162/04, 1986.

Primary Examiner—Teddy S. Gron
Attorney, Agent, or Firm—George M. Gould; Bernard S. Leon; George W. Johnston

[57] ABSTRACT

There is described compounds of the formula

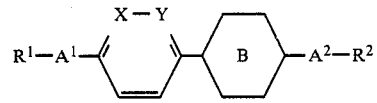

I wherein X stands for CH and Y stands for N or X stands for N and Y stands for CH; $A^1$ and $A^2$ signify single covalent bonds or one of the groups $A^1$ and $A_2$ also signifies trans-1,4-cyclohexylene, cis-4-cyano-trans-1,4-cyclohexylene or 1,4-phenylene optionally substituted with halogen or methyl; ring B represents trans-1,4-cyclohexylene, 1,4-phenylene optionally substituted with halogen or methyl or, when $A^2$ signifies a single covalent bond, also cis-4-cyano-trans-1,4-cyclohexylene; $R^1$ denotes an optionally halogen-substituted alkyl or alkenyl group in which optionally one $CH_2$ group or two non-adjacent $CH_2$ groups is/are replaced by —O—, —COO— and/or —OOC—; $R^2$ signifies an optionally halogen-substituted alkyl or alkenyl group in which optionally one $CH_2$ group or two non-adjacent $CH_2$ groups is/are replaced by —O—, —COO— and/or —OOC— or $R^2$ on a benzene ring also signifies —NCS, cyano or halogen; with the proviso that $R^1$ denotes an optionally halogen-substituted alkenyl group in which optionally one $CH_2$ group or two non-adjacent $CH_2$ groups is/are replaced by —O—, —COO— and/or —OOC— when $R^2$ signifies cyano or halogen; and with the proviso that $R^1$ and/or $R^2$ has a chiral carbon atom when $R^1$ and $R^2$ stand for optionally halogen-substituted alkyl groups in which optionally one $CH_2$ group or two non-adjacent $CH_2$ groups is/are replaced by —O—, —COO— and/or —OOC—, as well as liquid crystalline mixtures and their use for electro-optical purposes.

9 Claims, No Drawings

FOREIGN PATENT DOCUMENTS

| | | | |
|---|---|---|---|
| 3545345 | 7/1987 | Fed. Rep. of Germany | 252/299.61 |
| 3600052 | 7/1987 | Fed. Rep. of Germany | 252/299.61 |
| 3601452 | 7/1987 | Fed. Rep. of Germany | 252/299.61 |
| 3701629 | 7/1987 | Fed. Rep. of Germany | 252/299.61 |
| 240385 | 10/1986 | German Democratic Rep. | 252/299.61 |
| 61-24571 | 2/1986 | Japan | 252/299.61 |
| 61-43172 | 3/1986 | Japan | 252/299.61 |
| 61-158957 | 7/1986 | Japan | 252/299.61 |
| 61-165370 | 7/1986 | Japan | 252/299.61 |
| 62-172089 | 7/1987 | Japan | 252/299.61 |
| 62-172090 | 7/1987 | Japan | 252/299.61 |
| 62-207257 | 9/1987 | Japan | 252/299.61 |
| 62-238265 | 10/1987 | Japan | 252/299.61 |
| 86/07085 | 12/1986 | PCT Int'l Appl. | 252/299.61 |
| 215345A | 8/1985 | United Kingdom | 252/299.61 |
| 2153345 | 8/1985 | United Kingdom | 252/299.61 |
| 8603769 | 7/1986 | World Int. Prop. O. | 252/299.61 |
| 8606401 | 11/1986 | World Int. Prop. O. | 252/299.61 |
| 8607085 | 12/1986 | World Int. Prop. O. | 252/299.61 |
| 8705017 | 8/1987 | World Int. Prop. O. | 252/299.01 |
| 8705018 | 8/1987 | World Int. Prop. O. | 252/299.61 |
| 8802018 | 3/1988 | World Int. Prop. O. | 252/299.61 |
| 8807992 | 10/1988 | World Int. Prop. O. | 252/299.61 |

PYRIDINE LIQUID CRYSTALLINE COMPOUNDS

BACKGROUND OF THE INVENTION

1. Field of the Invention

The present invention is concerned with novel pyridine derivatives, liquid cyrstalline mixtures which contain these pyridine derivatives as well as their use for electro-optical purposes.

2. Description

Liquid cyrstals are used primarily as dielectrics in indicating devices, as the optical properties of such substances can be influenced by an applied voltage. Electro-optical devices based on liquid crystals are well-known to the person skilled in the art and can be based on various effects such as, for example, dynamic scattering, the deformation of aligned phases (DAP cells), the Schadt-Helfrich effect (twisted-nematic cells), the guest/host effect (guest/host cells). Most of the commercial indicating devices are based on the Schadt-Helfrich effect with a twisted nematic structure.

The liquid crystals which are used must have a good chemical and thermal stability and a good stability towards electrical fields and electromagnetic radiation. Further, the liquid crystals should be colourless, should have short response times and low viscosities, should give a high contrast and should possess a suitable mesophase, for example a nematic, cholesteric or chiral smectic, preferably a smectic C, F or I, phase in the usual operating temperatures. As liquid crystals are usually used as mixtures, it is, moreover, important that the components have a good miscibility with one another. Further properties, such as, for example, the electrical conductivity, the threshold potential, the dielectric anisotropy and the optical anisotropy must fulfill different requirements depending on the type of cell which is used.

Indicating devices having a high density of information (e.g. in computer terminals) have recently been used to an increasing extent. In order to keep the required connections small, the multiplex control has been further developed. Liquid crystals having improved multiplexibility and at the same time steep transmission curves are, however, required for this purpose.

The indicating devices mentioned earlier generally have response times in the order of several milliseconds or more.

In order to improve the response times there have also recently been used liquid crystals having ferroelectric properties. Chiral smectic phases, preferably smectic C phases, are used in this application. Hitherto, however, only a few of such liquid crystals have been known and the mesophase ranges are mostly narrow or lie at a relatively high temperature. Further, the stability of these liquid crystals is often unsatisfactory.

SUMMARY OF THE INVENTION

The present invention provides 2,5-disubstituted pyridines of the formula

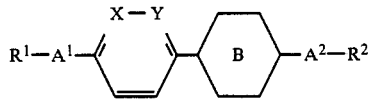

I wherein X stands for CH and Y stands for N or X stands for N and Y stands for CH; $A^1$ and $A^2$ signify single covalent bonds or one of the groups $A^1$ and $A^2$ also signifies trans-1,4-cyclohexylene, cis-4-cyano-trans-1,4-cyclohexylene or 1,4-phenylene optionally substituted with halogen or methyl; ring B represents trans-1,4-cyclohexylene, 1,4-phenylene optionally substituted with halogen or methyl or, when $A^2$ signifies a single covalent bond, also cis-4-cyano-trans-1,4-cyclohexylene; $R^1$ denotes an optionally halogen-substituted alkyl or alkenyl group in which optionally one $CH_2$ group or two non-adjacent $CH_2$ groups is/are replaced by —O—, —COO— and/or —OOC—; $R^2$ signifies an optionally halogen-substituted alkyl or alkenyl group in which optionally one $CH_2$ group or two non-adjacent $CH_2$ groups is/are replaced by —O—, —COO— and/or —OOC— or $R^2$ on a benzene ring also signifies —NCS, cyano or halogen; with the proviso that $R^1$ denotes an optionally halogen-substituted alkenyl group in which optionally one $CH_2$ group or two non-adjacent $CH_2$ groups is/are replaced by —O—, —COO— and/or —OOC— when $R^2$ signifies cyano or halogen; and with the proviso that $R^1$ and/or $R^2$ has a chiral carbon atom when $R^1$ and $R^2$ stand for optionally halogen-substituted alkyl groups in which optionally one $CH_2$ group or two non-adjacent $CH_2$ groups is/are replaced by —O—, —COO— and/or —COO—.

A preferred aspect comprises those compounds of formula I in which X stands for CH and Y stands for N or X stands for N and Y stands for CH; ring B represents trans-1,4-cyclohexylene or 1,4-phenylene optionally substituted with halogen or methyl; $A^1$ and $A^2$ signify single covalent bonds or one of the groups $A^1$ and $A^2$ also signifies trans-1,4-cyclohexylene or 1,4-phenylene optionally substituted with halogen or methyl; $R^1$ denotes alkyl or alkenyl in which optionally one $CH_2$ group or two non-adjacent $CH_2$ groups is/are replaced by oxygen and $R^2$ signifies alkenyl in which optionally one $CH_2$ group or two non-adjacent $CH_2$ groups is/are replaced by oxygen or $R^2$ on a benzene ring also signifies —NCS; or $R^1$ denotes alkenyl in which optionally one $CH_2$ group or two non-adjacent $CH_2$ groups is/are replaced by oxygen and $R^2$ signifies alkyl in which optionally one $CH_2$ group or two non-adjacent $CH_2$ groups is/are replaced by oxygen, or $R^2$ on a benzene ring also signifies cyano or halogen.

The compounds in accordance with the invention possess the required good stability and are colourless and have good miscibility with other liquid crystals. Further, the compounds in accordance with the invention posses short response times, low viscosities and an improved mesophase behavior. Furthermore, the compounds in accordance with the invention make possible low threshold potentials and, on the basis of the favorable ratio of the elastic constants $k_{33}$ (bend) and $k_{11}$ (splay), very steep transmission curves.

DETAILED DESCRIPTION OF THE INVENTION

The present invention describes 2,5-disubstituted pyridines of the formula

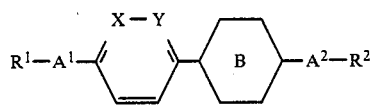

I wherein X is CH and Y is N or X is N and Y is CH; $A^1$ and $A^2$ each are single covalent bonds or one of $A^1$ an $A^2$ also can be trans-1,4-cyclohexylene, cis-4-cyano-trans-1,4-cyclohexylene or 1,4-phenylene which phenylene group is unsubstituted or optionally substituted with halogen or methyl; ring B is trans-1,4-cyclohexylene or 1,4-phenylene which phenylene group is unsubstituted or substituted with halogen or methyl or, when $A^2$ is a single covalent bond, ring B also can be cis-4-cyano-trans-1,4 cyclohexylene; $R^1$ is unsubstituted alkyl, unsubstituted alkenyl, halogen-substituted alkenyl, said unsubstituted or substituted alkyl or alkenyl optionally can have one of its $CH_2$ groups or two of its non-adjacent $CH_2$ groups replaced by at least one of —O—, —COO— and —OOC—; $R_2$ is unsubstituted alkyl, unsubstituted alkenyl, halogen-substituted alkyl or halogen-substituted alkenyl, said unsubstituted or substituted alkyl or alkenyl optionally can have one of its $CH_2$ groups or two of its non-adjacent $CH_2$ groups replaced by at least one of —O—, —COO— and —OOC, or when $R^2$ is positioned on a benzene ring $R^2$ also can be —NCS, cyano or halogen; with the proviso that $R^1$ is unsubstituted alkenyl or halogen-substituted alkenyl in which optionally one of its $CH_2$ groups or two of its non-adjacent $CH_2$ groups can be replaced by at least one of —O—, —COO— and —OOC— when $R_2$ is cyano or halogen; and with the further proviso that at least one of $R^1$ and $R^2$ has a chiral carbon atom when $R^1$ and $R^2$ both are unsubstituted alkyl or halogen-substituted alkyl in which optionally one of its $CH_2$ groups or two of its non-adjacent $CH_2$ groups can be replaced by at least one of —O—, COO— and —OOC—.

A preferred aspect comprises those compounds of formula I in which X is CH and Y is N, or X is N and Y is CH; ring B is trans-1,4-cyclohexylene or 1,4-phenylene which phenylene ring is unsubstituted or substituted with halogen or methyl; $A^1$ and $A^2$ each are single covalent bonds or one of $A^1$ and $A^2$ also can be trans-1,4-cyclohexylene or 1,4-phenylene which phenylene ring is unsubstituted or optionally substituted with halogen or methyl; $R^1$ is alkyl or alkenyl in which optionally one $CH_2$ group or two non-adjacent $CH_2$ groups can be replaced by oxygen and $R^2$ is alkenyl in which optionally one $CH_2$ group or two non-adjacent $CH_2$ groups can be replaced by oxygen, or when $R^2$ is positioned on a benzene ring $R^2$ also can be —NCS; or $R^1$ is alkenyl in which optionally one $CH_2$ group or two non-adjacent $CH_2$ groups can be replaced by oxygen and $R^2$ is alkyl in which optionally one $CH_2$ group or two non-adjacent $CH_2$ groups can be replaced by oxygen, or when $R^2$ is positioned on a benzene ring $R^2$ also can be cyano or halogen.

The compounds in accordance with the invention possess the required good stability and are colourless and have good miscibility with other liquid crystals. Further, the compounds in accordance with the invention possess short response times, low viscosities and an improved mesophase behavior. Furthermore, the compounds in accordance with the invention make possible low threshold potentials and, on the basis of the favorable ratio of the elastic constants $k_{33}$ (bend) and $k_{11}$ (splay), very steep transmission curves.

The compounds of formula I in which $R^2$ is cyano or —NCS possess large positive values of the dielectric anistropies. In the inventive compounds the cis-4-cyano-trans-1,4-cyclo-hexylene group lowers the values of the dielectric anisotropies and generally leads to large negative values of the dielectric anisotropies. The remaining compounds of formula I possess small absolute values of the dielectric anisotropies.

The cyano- and NCS-compounds with a straight-chain group $R^1$ as well as the compounds with straight-chain groups $R^1$ and $R^2$ are primarily suitable as components for nematic mixtures as well as, in combination with optically active additives, for cholesteric mixtures. The compounds of formula I with non-polar residues $R^1$ and $R^2$, especially the optically active compounds which have a chiral carbon atom in $R^1$ and/or $R^2$, are primarily suitable for liquid crystals with ferroelectric properties. The optically active compounds are, however, also suitable as optically active additives for cholesteric mixtures.

The term "1,4-phenylene optionally substituted with halogen or methyl" embraces in the scope of the present invention the groups 1,4-phenylene, 2-fluoro-1,4-phenylene, 2-chloro-1,4-phenylene, 2-bromo-1,4-phenylene and 2-methyl-1,4-phenylene. The term "benzene ring" relates to these groups. 1,4-Phenylene is preferred The transition temperatures, the solubility, the dielectric anisotropy and the like of the invention compounds can be modified, if desired, by using substituted groups.

As used herein, "alkyl" and "alkenyl" denote straight and branch chain groups of 1 to 20 carbon atoms. Suitable alkyl groups include methyl, ethyl, propyl, isopropyl, butyl, pentyl and the like. Suitable alkenyl groups include vinyl, propenyl, butenyl, pentenyl, hexenyl and the like.

The term "halogen" embraces fluorine, chlorine or bromine.

The term "cis-4-cyano-trans-1,4-cyclohexylene" denotes a cyclohexyl ring which has an axial (cis) cyano group in the 4-position, whereby the residue $R^1$ or $R^2$ in accordance with formula I is disposed equatorially (trans) in the 4-position. The compounds of formula I in which $A^1$, $A^2$ or ring B signifies cis-4-cyano-trans-1,4-cyclohexylene accordingly contain the grouping cis-4-cyano-trans-4-$R^1$-cyclohexyl or cis-4-cyano-trans-4-$R^2$-cyclohexyl.

The term "optionally halogen-substituted alkyl group in which optionally one $CH_2$ group or two non-adjacent $CH_2$ groups is/are replaced by —O—, —COO— and/or —OOC—" embraces straight-chain and branched groups such as alkyl, alkoxy, alkoxyalkyl, alkoxyalkoxy, alkanoyloxy, alkoxycarbonyl, halogenoalkyl, halogenoalkoxy, halogenoalkanoyloxy and the like.

The term "optionaly halogen-substituted alkenyl group in which optionally one $CH_2$ group or two non-adjacent $CH_2$ groups is/are replaced by —O—, —COO— and/or —OOC—" embraces straight-chain and branched groups such as alkenyl, alkenyloxy, alkoxyalkenyl, alkenyloxyalkyl, alkoxyalkenyloxy, alkenoyloxy, alkenyloxycarbonyl, halogenoalkenyl, halogenoalkenyloxy and the like.

A preferred group of compounds in accordance with the invention comprises the compounds of formula I in which $R^2$ is —NCS, especially the compounds of the formula

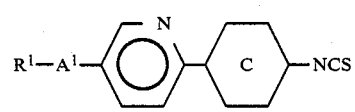

Ia wherein $R^1$ has the above significance and preferably is alkyl or alkenyl in which optionally one $CH_2$ group or two non-adjacent CH$_2$ groups therein can be replaced by oxygen; A$^1$ is a single covalent bond, trans-1,4-cyclohexylene or 1,4-phenylene which phenylene ring is unsubstituted or optionally substituted with halogen or methyl; and ring C is 1,4-phenylene which is unsubstituted or substituted with halogen or methyl.

These compounds have comparatively large mesophase ranges and a large positive dielectric anisotropy. They are especially suitable for use in twisted-nematic cells and give steep transmission curves and short response times. R$^1$ is preferably a straight-chain residue of the groups described above.

Further, there are preferred compounds of formula I having a terminal cyano group (R$_2$=cyano), especially those in which R$^2$ is cyano, A$^2$ is a single covalent bond, ring B is 1,4-phenylene which is unsubstituted or substituted with halogen or methyl, Y is N, X is CH and A$^1$ is a single covalent bond, trans-1,4-cyclohexylene or 1,4-phenylene which phenylene ring is unsubstituted or optionally substituted with halogen or methyl. R$^1$ preferably is the preferred unsaturated residues in formula Ia as described above. These compounds are intermediates for the compounds of formula I in which R$^2$ signifies —NCS and R$^1$ has a C—C double bond and are also liquid crystals having a large dielectric anisotropy, favorable elastic constants and improved mesophase behavior.

A further preferred aspect of the present invention comprises the compounds of formula I in which R$^1$ and R$^2$ denote unsubstituted alkyl or alkenyl or halogen-substituted alkyl or alkenyl in which optionally one CH$_2$ group or two non-adjacent CH$_2$ groups can be replaced by at least one of —O—, —COO— and —OOC—. A preferred group of such compounds comprises those in which A$^1$ and A$^2$ signify covalent bonds or one of the groups A$^1$ and A$^2$ also signifies trans-1,4-cyclohexylene or 1,4-phenylene which phenylene ring is unsubstituted or substituted with halogen or methyl, one of the residues R$^1$ and R$^2$ denotes alkenyl in which optionally one CH$_2$ group or two non-adjacent CH$_2$ groups can be replaced by oxygen and the other of the residues R$^1$ and R$^2$ denotes alkyl or alkenyl in which optionally one CH$_2$ group or two non-adjacent CH$_2$ groups can be replaced by oxygen. These compounds have small absolute values of the dielectric anisotropies or, in the case of the axial nitriles, a negative dielectric anisotropy. Further, they have comparatively low viscosities and favorable elastic constants and permit low threshold potentials. The optically inactive compounds are especially suitable as non-polar or negative dielectric components of nematic or cholesteric dielectrics for twisted-nematic cells, guest/host cells, phase change cells etc. The optically active compounds are especially suitable for ferroelectric applications. However, optically inactive compounds can also be used, if desired, in ferroelectric mixtures. Further, optically active compounds can also be used as chiral additives in twisted-nematic cell applications, phase change applications and the like.

A preferred group of compounds in accordance with the invention especially for ferroelectric applications comprises the optically active compounds of the general formula

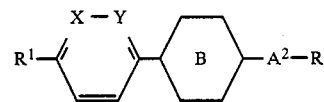

wherein R$^1$, X, Y and ring B have the significances given in formula I; A$^2$ signifies a single covalent bond, trans-1,4-cyclohexylene, cis-4-cyano-trans-1,4-cyclohexylene or 1,4-phenylene which phenylene ring is unsubstituted or substituted with halogen or methyl; and R denotes unsubstituted alkyl or alkenyl or halogen-substituted alkyl or alkenyl in which optionally one CH$_2$ group or two non-adjacent CH$_2$ groups of the unsubstituted or substituted alkyl or alkenyl group can be replaced by at least one of —O—, —COO— and —OOC—; with the proviso that at least one of R$^1$ and R has a chiral carbon atom.

The compounds of formula Ii are especially suitable as components of mixtures with ferroelectric properties and themselves have to a large extent suitable chiral smectic phases. Ring B in formula Ii above preferably stands for 1,4-phenylene optionally substituted with halogen or methyl, especially for 1,4-phenylene. With the inventive compounds, the tendency to form chiral smectic phases is surprisingly generally increased further by the presence of a double bond. Therefore, preferably R$^1$ and/or R in formula Ii has a double bond. Especially stable chemically are primarily those compounds of formula Ii in which one of the residues R$^1$ and R denotes alkenyl in which optionally one CH$_2$ group or two non-adjacent CH$_2$ groups can be replaced by oxygen and the other of the residues R$^1$ and R denotes alkyl or alkenyl in which optionally one CH$_2$ group or two non-adjacent CH$_2$ groups can be replaced by oxygen.

The optically inactive compounds corresponding to formula Ii without a chiral carbon atom in R$^1$ and R, but with at least one C—C double bond in at least one of R$^1$ and R are also suitable as components of ferroelectric mixtures. In this case the mixtures preferably contain at least one chiral additive.

A preferred group of non-polar or negative dielectric compounds in accordance with the invention especially for nematic and cholesteric applications comprises the compounds of the formula

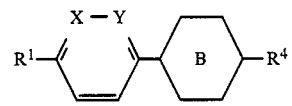

wherein one of the residue R$^3$ and R$^4$ denotes unsubstituted alkenyl or halogen-substituted alkenyl in which optionally one CH$_2$ group or two non-adjacent CH$_2$ groups of the unsubstituted or substituted alkenyl can be replaced by at least one of —O—, —COO— and —OOC; the other of the residues R$^3$ and R$^4$ denotes an unsubstituted alkyl or alkenyl or optionally halogen-substituted alkyl or alkenyl in which optionally one CH$_2$ group or two non-adjacent CH$_2$ groups of such moiety can be replaced by at least one of —O—, —COO— and —OOC—; and X, Y and ring B have the significance given in formula I.

The compounds of formula Ib are low-viscous compounds with particularly favorably elastic constants and, in spite of small absolute values of the dielectric anisotropies, they permit low threshold potentials. Preferably, ring B in formula Ib represents trans-1,4-cyclohexylene or 1,4-phenylene optionally substituted with halogen or methyl. Further, there are preferred those compounds of formula Ib in which one of the residues $R^3$ and $R^4$ denotes alkenyl in which optionally one $CH_2$ group or two non-adjacent $CH_2$ groups is/are replaced by oxygen and the other of the residues $R^3$ and $R^4$ denotes alkyl or alkenyl in which optionally one $CH_2$ group or two non-adjacent $CH_2$ groups is/are replaced by oxygen.

The variation of the position of the double bond in formula Ib permits a further optimization of the electro-optical and mesomorphoic properties. For example, the compounds in which $R^3$ and/or $R^4$ signifies 1E-alkenyl, 2E-alkenyloxy, 3E-alkenyl, 4-alkenyloxy or 5-alkenyl have especially favorable mesophase ranges and short response times. On the other hand, for example, the compounds of formula Ib in which at least one of $R^3$ and $R^4$ is 2Z-alkenyl, 3-alkenyloxy or 4-alkenyl have especially low ratios of the elastic constants $k_{33}$ and $k_{11}$ and give especially low threshold potentials.

The tricyclic compounds, i.e. the compounds of formula I in which $A^1$ or $A^2$ signifies trans-1,4-cyclohexylene, cis-4-cyano-trans-1,4-cyclohexylene or 1,4-phenylene optionally substituted with halogen or methyl, possess high clearing points and likewise given steep transmission curves.

In formulae I, Ii and Ib above, preferably X stands for CH and Y stands for N. Ring B in formulae I and Ib preferably denotes trans-1,4-cyclohexylene or 1,4-phenylene and ring C in formula Ia preferably denotes 1,4-phenylene.

Preferred optionally halogen-substituted alkyl and alkenyl groups $R^1$, $R^2$, $R^3$, $R^4$ and R in which optionally one $CH_2$ group or two non-adjacent $CH_2$ groups is/are replaced by $-O-$, $-COO-$ and/or $-OOC-$ are the groups mentioned above, particularly the especially stable alkyl and alkenyl groups, in which optionally one $CH_2$ group or two non-adjacent $CH_2$ groups has been replaced by oxygen.

Preferred alkyl and alkenyl groups in which optionally one $CH_2$ group of two non-adjacent $CH_2$ groups can be replaced by oxygen are alkyl, alkoxy, alkoxyalkyl, alkoxyalkoxy, alkenyl, alkenyloxy, alkoxyalkenyl, alkoxyalkenyloxy and alkenyloxyalkyl, especially alkyl, alkoxy, alkenyl and alkenyloxy. Preferably, a double bond optionally present in $R^1$ and/or $R^2$ is in position 1, 3 or 4 (including oxygen atoms which may be present) of the side-chain $R^1$ or $R^2$, especially in position 4. Especially preferred unsaturated groups are therefore groups such as 1E-alkenyl, 3E-alkenyl, 4-alkenyl, 2E-alkenyloxy, 3-alkenyloxy, alkoxy-3E-alkenyl, alkoxy-4-alkenyl, alkoxy-3-alkenyloxy and the like. Preferably, therefore, $R^1$ and/or $R^2$ in formula I, $R^1$ in formula Ia, $R^1$ and/or R in formula Ii and $R^3$ and/or $R^4$ in formula Ib stands for the aforementioned groups.

The residues $R^1$ and $R^2$ conveniently have, in general, a maximum of 18 carbon atoms in each case. Straight-chain groups $R^1$ or $R^2$ preferably have 1-12 carbon atoms in each case and particularly 1-7 carbon atoms in each case. Groups $R^1$ or $R^2$ with chiral carbon atoms preferably have 4-18 carbons atoms and particularly 4-15 carbon atoms.

Optically active compounds of formula I or Ii for ferroelectric applications contain in $R^1$ and $R^2$ together preferably at least 10, especially at least 12, carbon atoms in the case of bicyclic compounds and preferably at least 8, especially at least 10, carbon atoms in the case of tricyclic compounds. This also applies in the use of achiral compounds for ferroelectric mixtures. Compounds with a smaller carbon number in $R^1$ and $R^2$ are, however, also suitable as chiral doping agents for cholesteric or chiral smectic mixtures.

Preferred groups with chiral carbon atoms are the groups of the formulae

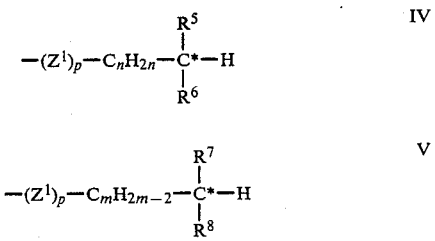

wherein m, n and p each are integers, p is 0 or 1, n is 0–6 and m is 2–6; $R^5$ is alkyl and $R^6$ is halogen, alkoxy, alkenyl, alkenyloxy, or alkyl which substituent for $R^6$ is different from that of $R^5$; or $R^5$ is alkenyl and $R^6$ is alkoxy; $R^7$ is alkyl and $R^8$ is halogen, alkoxy or alkyl which substituent for $R^8$ is different from that of $R^7$; and $Z^1$ is $-CH_2-$, $-O-$, $-COO-$ or $-OOC-$.

In formulae IV and V above $Z^1$ preferably stands for oxygen. Especially preferred chiral residues are the groups of formulae IV and V in which $R^5$ or $R^7$ denotes methyl and $R^6$ or $R^8$ denotes alkyl different from methyl, especially ethyl.

Especially preferred optically active compounds of formula I or Ii are those in which one of the residues $R^1$ and $R^2$ or one of the residues $R^1$ and R denotes a chiral group of formula IV or V and the other of the residues $R^1$ and $R^2$ or the other of the residues $R^1$ and R signifies a straight-chain alkyl, alkoxy, alkenyl or alkenyloxy group or a chiral group of formula IV or V.

The compounds of formula I can be manufactured according to methods known per se, for example according to the methods illustrated in Schemes 1-3 hereinafter in which $A^1$, $A^2$, X, Y and ring B have the significance given in formula I, Ts means p-tosyl, $R^1$ and $R^{11}$ denote optionally halogen-substituted alkyl or alkenyl groups in which optionally one $CH_2$ group or two non-adjacent $CH_2$ groups can be replaced by oxygen and $R^9$ and $R^{10}$ signify in which optionally one $CH_2$ group or two non-adjacent $CH_2$ groups can be replaced by oxygen or $R^{10}$ also signifies halogen.

Scheme 1

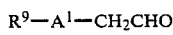

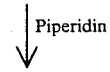

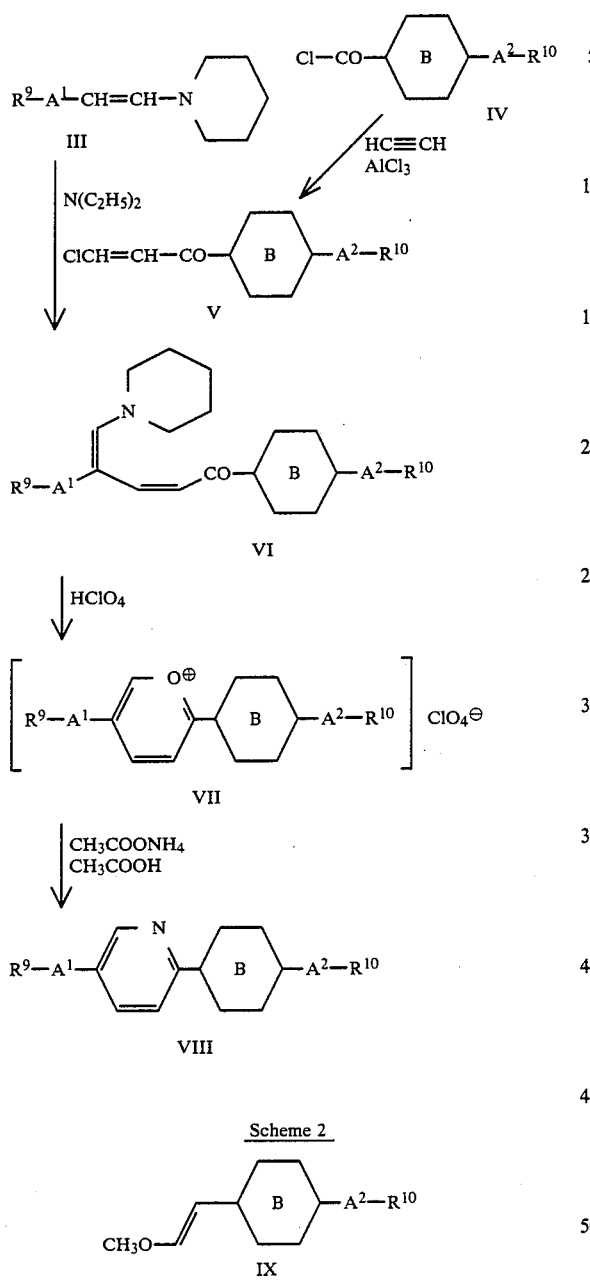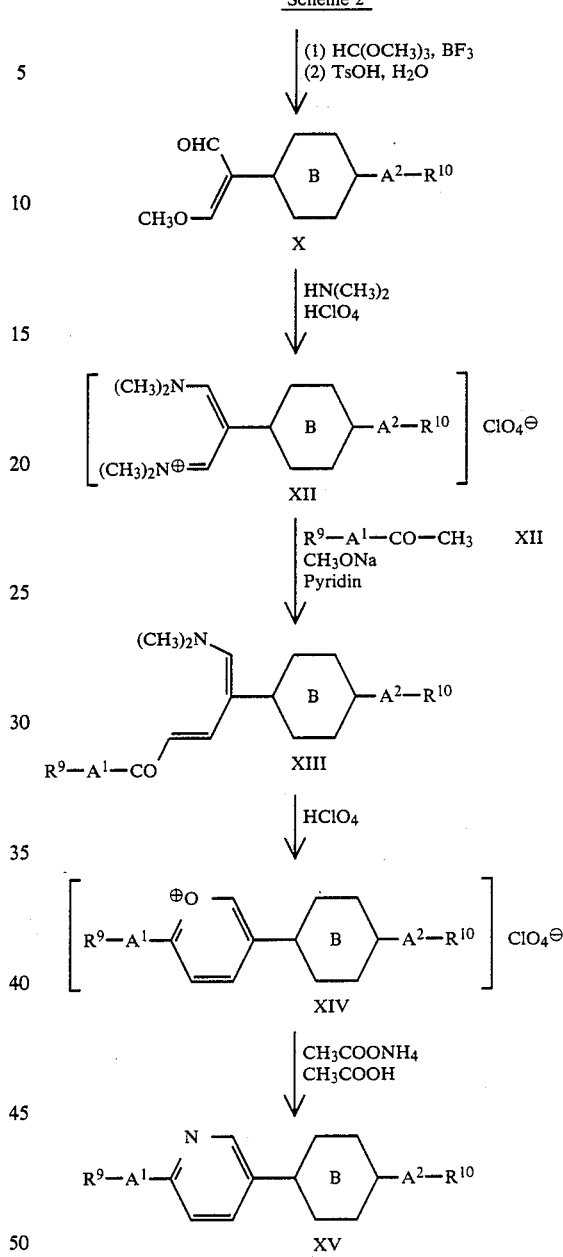

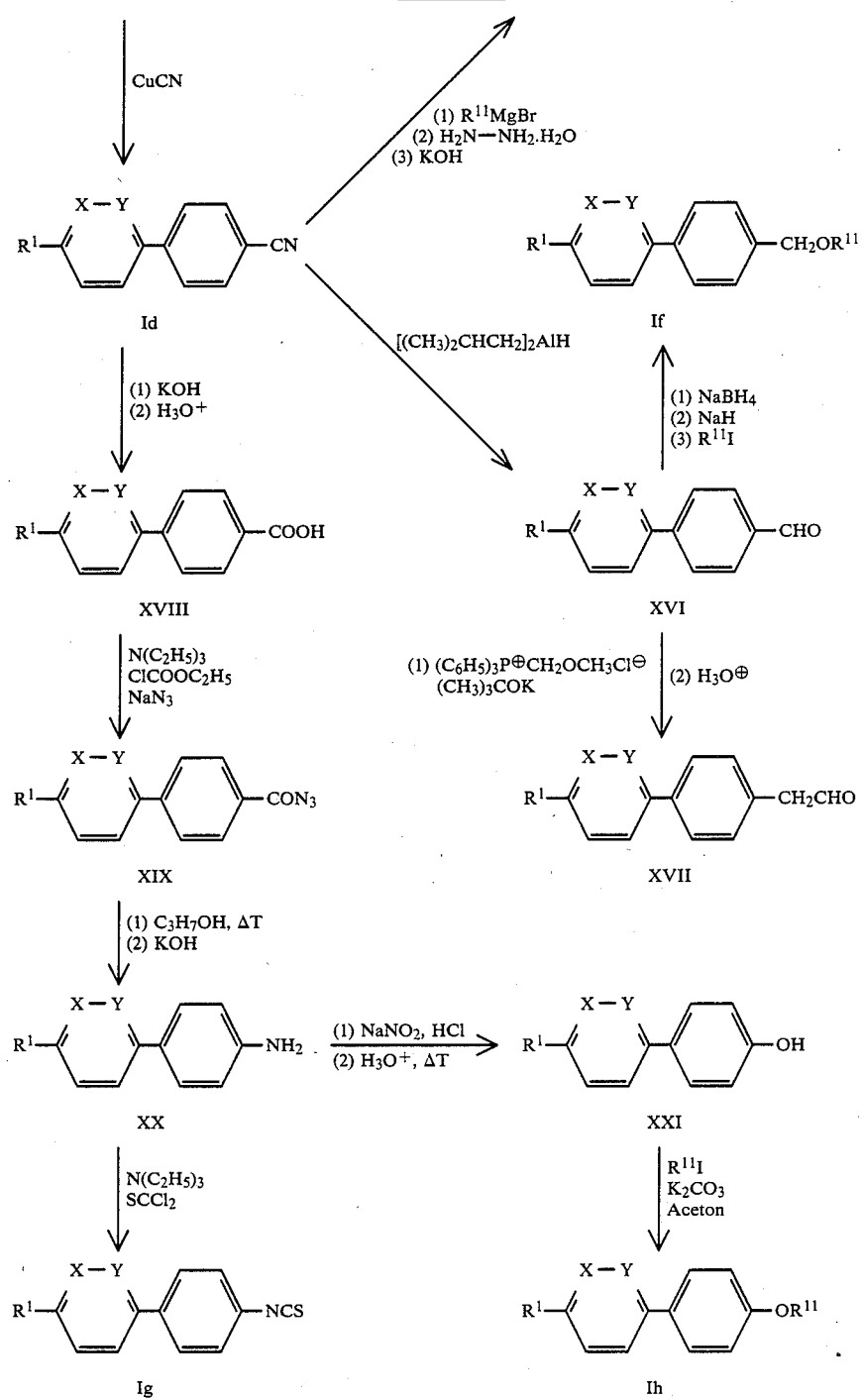

Scheme 3

The starting materials of formulae II, IV, IX and XII are known or are analogues of known compounds and can be prepared according to known methods, for example from the corresponding nitriles. The aldehydes of formula II can be obtained, for example, from the corresponding or homologous nitriles by reaction with diisobutylaluminium hydride and optional subsequent conversion into homologous aldehydes by reaction with methoxymethyl-triphenylphosphonium chloride and hydrolysis of the resulting enol ether with acid. The acid chlorides of formula IV can be obtained, for example, from the corresponding nitriles by hydrolysis and subsequent reaction of the resulting carboxylic acids with thionyl chloride. The methoxyvinyl compounds of formula IX can be obtained, for example, from the corresponding nitriles by reduction with diisobutylaluminium hydride and subsequent reaction of the resulting aldehydes with methoxyvinyl-triphenylphosphonium chloride. The methyl ketones of formula XII can be obtained, for example, from the corresponding nitriles by reaction with methylmagnesium bromide.

The tricyclic commpounds of formula I can also be manufactured in an analogous manner to the methods illustrated in Scheme 3.

For the manufacture of the compounds of formula I which have a C—C double bond in $R^1$ and/or $R^2$, there are conveniently used as starting materials, in place of the unsaturated compounds corresponding to formula II, IV, IX and XII, those aldehydes, acid chlorides, methoxyvinyl compounds or methyl ketones which have the group >CBr—CBr< or a protected hydroxymethylene group, e.g. the group $CH_3COOCH<$ or $p—CH_3O—C_6H_4—OCH<$, in place of the double bond.

The required brominated compounds, i.e. the compounds corresponding to formulae II, IV, IX and XII which have two vicinal bromine substituents in $R^9$ and $R^{10}$, can be prepared from the corresponding brominated nitriles in an analogous manner to the methods described above. The brominated nitriles can be obtained from the corresponding unsaturated nitriles, e.g. by reaction with bromine in chloroform.

The required compounds with a protected hydroxymethyl group can also be prepared according to methods known per se. The required acetates can be obtained, for example, from the corresponding cyanoaldehydes, e.g. by reduction of the formyl group to the hydroxymethyl group by means of sodium borohydride or catalytic hydrogenation, subsequent reaction of the nitrile group in an analogous manner to the methods given above and acetylation of the hydroxymethyl group with acetyl chloride or acetic anhydride. The p-methoxyphenolates can be obtained, for example, from the corresponding cyanoaldehydes, e.g. by reduction of the formyl group to the hydroxymethyl group by means of sodium borohydride or catalytic hydrogenation, subsequent etherification of the hydroxymethyl group with p-methoxyphenol according to the method described in Tetrahedron Letters 26, 2691 (1985) and reaction of the nitrile group in an analogous manner to the methods given above.

The conversion of the dibromides into unsaturated compounds is conveniently effected after the synthesis of the pyridine ring, i.e. on the dibromides corresponding to formulae VIII and XV. The conversion can be effected in a manner known per se, for example with zinc in glacial acetic acid.

The conversion of the protected hydroxymethyl group into a group with a C—C double bond is also conveniently effected after the synthesis of the pyridine ring, whereby the acetate group can already be hydrolzed during the reaction with perchloric acid. The conversion can be effected according to methods known per se, for example by hydrolysis of the acetate group or by oxidative removal of the n-methoxyphenolate group with cer-(IV) ammonium nitrate in acetonitrile/water, conversion of the hydroxymethyl group into the formyl group with oxalyl chloride in dimethyl sulphoxide and reaction of the aldehydes obtained with Wittig reagents, e.g. with an alkyl-triphenylphosphonium bromide. If desired, prior to the Wittig reaction the aldehydes can be converted into homologous aldehydes by reaction with methoxymethyl-triphenylphosphonium chloride and subsequent hydrolysis of the enol ether with acid.

If desired, the intermediates with a hydroxymethyl group, obtained after the cleavage of the protecting group, can also, in a manner known per se, be alkylated with an alkyl iodide, alkenyl iodide etc, be esterified with an alkanoic acid, alkenoic acid etc or, after oxidation to the carboxylic acid, be esterified with an alkanol, alkenol etc to give compounds of formula I in which $R^1$ and/or $R^2$ has a group —O—, —COO— or —OOC—.

Compounds of formula I with a C—C double bond in $R^2$ can also be obtained according to the methods illustrated in Scheme 3.

If desired, the aldehydes of formula XVII can be converted into further homologous aldehydes by successive chain-lengthening. Compounds XVI and XVII and homologues of these compounds can be converted by reaction with Wittig reagents, e.g. with an alkyl-triphenylphosphonium bromide, into compounds of formula I which have a C—C double bond in $R^2$, or can be reduced with sodium borohydride and the resulting alcohols can be etherified (analogously to reaction XVI→If).

The compounds of formula I which have a cis-4-cyano-trans-1,4-cyclohexylene group can also be obtained in a manner known per se from the corresponding 4-cyanocyclohexyl compounds by reaction with an alkyl bromide, alkyl iodide, alkenyl bromide and the like in the presence of a base. The 4-cyanocyclohexyl compounds can be prepared according to methods known per se, for example from the corresponding 4-formylcyclohexyl compounds by reaction with hydroxylamine hydrochloride and pyridine.

The compounds in accordance with the invention can be used in the form of mixtures with one another and/or with other liquid crystal components such as e.g. with substances from the classes of Schiff's bases, azobenzenes, azoxybenzenes, phenylbenzoates, cyclohexanecarboxylic acid phenyl esters, cyclohexanecarboxylic acid cyclohexyl esters, biphenyls, phenylcyclohexanes, phenylpyrimidines, cyclohexylpyrimidines, phenyldioxanes, 2-cyclohexyl-1-phenylethanes and the like. Such substances are known to the person skilled in the art and many of them are, moreover, commercially obtainable.

On the basis of the favorable properties of the compounds in accordance with the invention, their amount in liquid crystalline mixtures can vary in wide limits and can amount to up to 100%. In general, the mixtures in accordance with the invention contain about 1–80 wt.%, preferably about 5–50 wt.%, of compounds of formula I. When chiral compounds of formula I are used as optically active additives for the production of cholesteric mixtures, the amount can also be smaller and can be, for example, about 0.2–50 wt.% depending on the pitch.

The liquid crystals mixtures in accordance with the invention which have nematic or cholesteric properties preferably contain, in addition to one or more compounds of formula I, one or more compounds of the following formulae

XXII

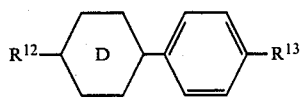

$R^{12}$—D—$R^{13}$

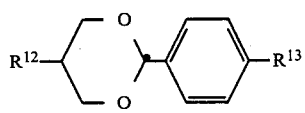 XXIII

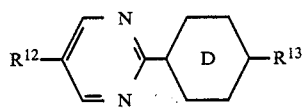 XXIV

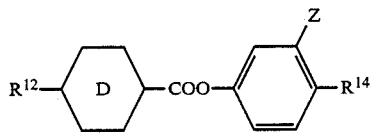 XXV

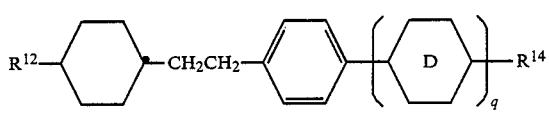 XXVI

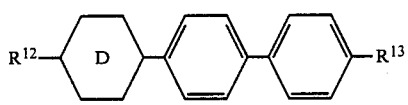 XXVII

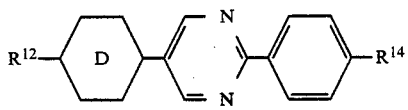 XXVIII

 XXIX

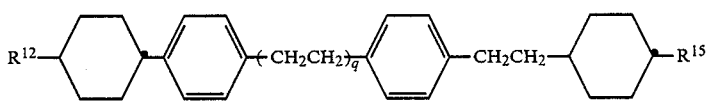 XXX

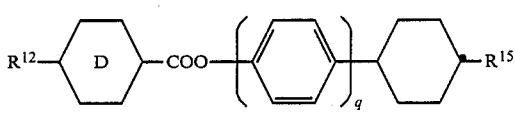 XXXII

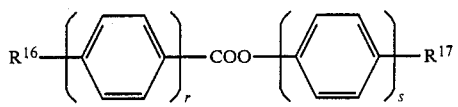 XXXI

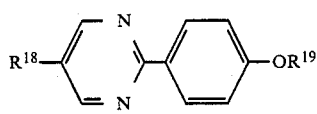 XXXIII wherein $R^{12}$, $R^{13}$, $R^{14}$ and $R^{15}$ each individually signify alkyl, alkoxy, alkenyl or alkenyloxy with 1 to 7 carbon atoms or $R^{13}$ on a benzene ring also signifies cyano or —NCS or $R^{14}$ on a benzene ring also signifies cyano; ring D represents trans-1,4-cyclohexylene or 1,4-phenylene; Z denotes hydrogen or fluorine; and q stands for the number 0 or 1.

The liquid crystal mixtures in accordance with the invention which have ferroelectric properties preferably contain, in addition to one or more compounds of formula I in which $R^2$ signifies an optionally halogen-substituted alkyl or alkenyl group in which optionally one $CH_2$ group or two non-adjacent $CH_2$ groups is/are replaced by —O—, —COO— and/or —OOC—, one or more compounds of the formulae wherein $R^{16}$ and $R^{17}$ signify alkyl, alkoxy, alkanoyl, alkanoyloxy, alkoxycarbonyl or alkoxycarbonyloxy; $R^{18}$ and $R^{19}$ represent alkyl; and r and s denote the numbers 1 or 2.

Preferably, one or more components of the ferroelectric mixture is optically active. Therefore, the use of optically active compounds of formula I with a chiral carbon atom in $R^1$ and/or $R^2$ is preferred. Preferred additives are the optically active compounds of formulae XXXI and XXXIII in which $R^{16}$ or $R^{17}$ or $R^{18}$ or $R^{19}$ as the case may be has a chiral carbon atom.

The mixtures in accordance with the invention can also contain dichroic colouring substances, for example azo, azoxy or anthraquinone colouring substances. The amount of colouring substance is determined by the solubility and the desired colour, extinction and the like and generally amounts to a maximum of about 10 wt.% in the total mixture.

The manufacture of the mixtures in accordance with the invention can be effected in a manner known per se, e.g. by heating a mixture of the constituents to a temperature barely above the clearing point and subsequently cooling down. The manufacture of an electro-optical device can also be effected in a manner known per se, e.g. by evacuating a suitable cell and introducing the mixture into the evacuated cell.

The manufacture of the compounds and mixtures in accordance with the invention is illustrated in more detail by the following Examples. The phases are denoted by the following symbols: C stands for crystalline, S stands for smectic, $S_A$ stands for smectic A, $S_C$ stands for smectic C, $S_c{}^*$ stands for chiral smectic C, N stands for nematic, Ch stands for cholesteric and I stands for isotropic. $p_o=(V_{50}-V_{10})/V_{10}$ is a measure for the steepness of the transmission curve, with $V_{10}$ and $V_{50}$ signifying the voltage for 10% and 50% transmission, respectively (in a twisted-nematic cell with 0° angle of tilt). Δn denotes the optical anisotropy. Temperature is in degrees Celsius (C.°) and room temperature is about 23° C. Unless otherwise stated percentages and ratios relating to solvent mixtures are expressed in volume, purity data determined by gas chromatography are expressed in area percent and the remaining percentages and ratios are expressed in weight. Unless indicated otherwise such as by use of other than past tense verbs, the Examples were carried out as written.

EXAMPLE 1

(a) A mixture of 3.026 g of 2-(cyanophenyl)-5-pentylpyridine, 125 ml of diethylene glycol and 13.8 g of potassium hydroxide was heated to 175° C. for 1.5 hours while stirring and gassing with nitrogen. The reaction mixture was then left to cool, adjusted to pH 8 with semi-concentrated hydrochloric acid and extracted with methylene chloride. The organic phase was washed with water, dried over sodium sulphate, filtered and concentrated. The crude p-(5-pentyl-2-pyridyl)benzoic acid obtained was recrystallized from acetone/hexane.

(b) A solution of 2.1 g of p-(5-pentyl-2-pyridyl)benzoic acid in 80 ml of acetone was cooled to 2° C. while stirring and gassing with nitrogen and treated dropwise within 10 minutes with a solution of 2.16 ml of triethylamine in 15 ml of acetone. The reaction mixture was then treated dropwise at 1°-2° C. within 10 minutes with a solution of 1.86 ml of ethyl chloroformate in 8 ml of acetone and stirred at this temperature for a further 30 minutes. Subsequently, a solution of 1.38 g of sodium azide in 8 ml of water was added dropwise to the reaction mixture at 1°-2° C. within 10 minutes and the resulting mixture was stirred for a further 1 hour in an ice-bath. Thereafter, the reaction mixture was poured into 200 ml of water and extracted with diethyl ether. The organic phase was washed with water, dried over sodium sulphate, filtered and freed from solvent. Purification of the resulting light yellowish crystals (2.1 g) by chromatography on 120 g of silica gel with 1 l of methylene chloride gave 2.15 g of p-(5-pentyl-2-pyridyl)benzoic acid azide as a light yellowish paste.

(c) 2.147 g of p-(5-pentyl-2-pyridyl)benzoic acid azide were dissolved in 60 ml of n-propanol under nitrogen and the solution was stirred at 140° C. for 45 minutes. After evaporation of the solvent on a rotary evaporator there were obtained 2.24 g of propyl p-(5-pentyl-2-pyridyl)phenylcarbamate as light yellowish crystals.

(d) A solution of 2.24 g of propyl p-(5-pentyl-2-pyridyl)phenylcarbamate in 186 ml of diethylene glycol was treated with 26 ml of potassium hydroxide and 47 ml of water and heated at 170° C. under nitrogen. After 1.75 hours the reaction mixture was cooled, poured into 250 ml of water and extracted with methylene chloride. The organic phase was dried over sodium sulphate, filtered and freed from solvent on a rotary evaporator under a vacuum. Purification of the residue (1.39 g) by chromatography on 60 g of silica gel with 1.5 l of methylene chloride and 0.5 l of methylene chloride/ethyl acetate (vol. 4:1) and subsequent recrystallization from methylene chloride/hexane gave 0.731 g of p-(5-pentyl-2-pyridyl)aniline as yellowish crystals; m.p. 60.3°–61.3° C.

(e) A solution of 1.256 g of p-(5-pentyl-2-pyridyl)aniline in 29 ml of chloroform was treated at 5° C. under nitrogen with 1.46 ml of triethylamine. Then, at 1° C. within 20 minutes a solution of 0.49 ml of 95 percent thiophosgene in 14.5 ml of chloroform was added dropwise to the reaction mixture so that the temperature did not exceed 3° C. The reaction mixture was subsequently stirred at room temperature for 45 minutes and under reflux for a further 40 minutes, then cooled and washed with 40 ml of 3N ammonia and with water. The aqueous phases were back-extracted with methylene chloride. The organic phases were dried over sodium sulphate, filtered and freed from solvent. Purification of the resulting brownish paste (1.56 g) by chromatography on 60 g of silica gel with 700ml of methylene chloride/hexane (vol. 1:1) and subsequent crystallization from diethyl ether/hexane gave 1.17 g of p-(5-pentyl-2-pyridyl)phenylisothiocyanate as colourless crystals with m.p. (C—$S_A$) 36.3° C. and cl.p. ($S_A$—I) 97.2° C.

The following compounds can be manfactured in an analogous manner:
p-(5-Propyl-2-pyridyl)phenylisothiocyanate,
p-(5-hexyl-2-pyridyl)phenylisothiocyanate; m.p. (C—$S_A$) 12.6° C., cl.p. ($S_A$—I) 99.0° C.,
p-(5-heptyl-2-pyridyl)phenylisothiocyanate,
p-[5-(3-butenyl)-2-pyridyl]phenylisothiocyanate,
p-[5-(3-E-pentenyl)-2-pyridyl]phenylisothiocyanate,
p-[5-(4-pentenyl)-2-pyridyl]phenylisothiocyanate,
p-[5-(4-ethylphenyl)-2-pyridyl]phenylisothiocyanate,
p-[5-(4-pentylphenyl)-2-pyridyl]phenylisothiocyanate,
p-[5-(4-(4-pentenyl)phenyl)-2-pyridyl]phenylisothiocyanate,
p-[5-(trans-4-ethylcyclohexyl)-2-pyridyl]phenylisothiocyanate,
p-[5-(trans-4-pentylcyclohexyl)-2-pyridyl]phenylisothiocyanate,
p-[5-(trans-4-(4-pentenyl)cyclohexyl)-2-pyridyl]phenylisothiocyanate.

EXAMPLE 2

A suspension of 5.59 g of 2-(p-bromophenyl)-5-(4-pentenyl)pyridine, 4 ml of dimethylformamide and 1.98 g of copper(I) cyanide was heated to 180° C. for 3 hours while stirring. The brown reaction mixture was then cooled to room temperature, subsequently poured into a mixture of 3.67 g of iron(III) chloride, 36.7 ml of water and 0.245 ml of concentrated hydrochloric acid and stirred at 55° C. for a further 1 hour. Thereafter, the mixture was cooled and partitioned between methylene chloride and water. The organic phase was washed with water, dried over sodium sulphate and filtered. The filtrate was evaporated and the residue was purified by chromatography on 250 g of silica gel with 2.5 l of methylene chloride under slight pressure. The p-[5-(4-pentenyl)-2-pyridyl]benzonitrile obtained had a m.p. (C—N) of −12° C. and could not be crystallized by cooling to below −70° C.

The following compounds can be manufactured in an analogous manner:
p-[5-(3-Butenyl)-2-pyridyl]benzonitrile,
p-[5-(3E-pentenyl)-2-pyridyl]benzonitrile,
p-[5-(4-(4-pentenyl)phenyl)-2-pyridyl]benzonitrile,
p-[5-(trans-4-(4-pentenyl)cyclohexyl)-2-pyridyl]benzonitrile.

EXAMPLE 3

(a) 10 ml of 3N sulphuric acid were treated while stirring with 1.8 g of p-(5-octyl-2-pyridyl)aniline. The mixture was cooled to 5° C. and then treated dropwise at 0°–5° C. within about 3 minutes with a solution of 0.442 g of sodium nitrite in 2 ml of water. The brown mixture obtained was poured into 100 ml of water and heated to reflux for 30 minutes while stirring. The reaction mixture was subsequently cooled to room temperature, adjusted to about pH 5 with 7 ml of 3N sodium hydroxide solution and extracted once with 200 ml of methylene chloride and once with 100 ml of methylene chloride. The organic phases were washed with 150 ml of dilute sodium chloride solution, dried over sodium sulphate and evaporated in a vacuum. The residue (1.867 g) was separated by chromatography on 250 g of silica gel at 0.4 bar with methylene chloride and methylene chloride/acetone. Recrystallization of the resulting red-brown oil in diethyl ether/hexane at 0° C. gave 0.635 g of p-(5-octyl-2-pyridyl)phenol as beige crystals. Working-up of the mother liquor gave 0.355 g of crude p-(5-octyl-2-pyridyl)phenol as a brown oil.

(b) A mixture of 0.355 g of crude p-(5-octyl-2-pyridyl)-phenol, 10 ml of ethanol, 0.260 g of (S)-6-methyloctyl bromide, 0.172 g of potassium carbonate and a spatula tip of sodium iodide was heated to 90° C. (oil bath temperature) for about 60 hours while stirring. The brown suspension obtained was subsequently cooled and concentrated in a vacuum. The brown oily residue was separated by chromatography on 120 g of silica gel at 0.4 bar with methylene chloride/acetone (vol. 99:1). The resulting brownish paste (0.367 g) was dissolved in about 5 ml of hexane, the solution was filtered and the filtrate was cooled to −25° C. The precipitate was filtered off under suction and distilled at 250° C/0.05 bar, there being obtained 0.122 g of (S)-2-[p-(6-methyloctyloxy)phenyl]-5-octylpyridine as a light yellowish smectic liquid crystal. Concentration of the mother liquor and subsequent distillation gave a further 0.164 g of (S)-2-[p-(6-methyloctyloxy)phenyl]-5-octylpyridine as a light yellowish smectic liquid crystal. The product (total 0.286 g) was treated with diethyl ether, evaporated, dried at 80° C. for 2 hours and again distilled, there being obtained 0.245 g of (S)-2-[p-(6-methyloctyloxy)phenyl]-5-octylpyridine; m.p. (C–S) 36.1° C., phase transition (S—$S_c^*$) 57° C., cl.p. ($S_c^*$—I) 70.4° C.

The following compounds can be manufactured in an analogous manner:
(S)-2-[p-(2-Methylbutyloxy)phenyl]-5-decylpyridine,
(S)-2-[p-(4-methylhexyloxy)phenyl]-5-octylpyridine,
(S)-2-[p-(4-methylhexyloxy)phenyl]-5-decylpyridine,
(S)-2-[p-(5-methyloctyloxy)phenyl]-5-decylpyridine,
(S)-2-[p-(6-methyloctyloxy)phenyl]-5-hexylpyridine, phase transition (S—$S_c^*$) 54.2° C., cl.p. ($S_c^*$—I) 63.3° C.,
(S)-2-[p-(6-methyloctyloxy)phenyl]-5-decylpyridine,
(S)-2-[p-(2-octyloxy)phenyl]-5-hexylpyridine,
(S)-2-[p-(2-octyloxy)phenyl]-5-octylpyridine, m.p. 27.2° C.,
(S)-2-[p-(2-octyloxy)phenyl]-5-decylpyridine,
(S)-2-[p-(2-hexyloxypropoxy)phenyl]-5-octylpyridine,
(S)-5-[p-(2-methylbutyloxy)phenyl]-2-decylpyridine,
(S)-5-[p-(4-methylhexyloxy)phenyl]-2-octylpyridine,
(S)-5-[p-(4-methylhexyloxy)phenyl]-2-decylpyridine,
(S)-5-[p-(6-methyloctyloxy)phenyl]-2-hexylpyridine,
(S)-5-[p-(6-methyloctyloxy)phenyl]-2-octylpyridine,
(S)-5-[p-(6-methyloctyloxy)phenyl]-2-decylpyridine,
(S)-5-[p-(2-octyloxy)phenyl]-2-hexylpyridine,
(S)-5-[p-(2-octyloxy)phenyl]-2-octylpyridine,
(S)-5-[p-(2-octyloxy)phenyl]-2-decylpyridine,
2-[p-(allyloxy)phenyl]-5-hexylpyridine,
2-[p-(2E-butenyloxy)phenyl]-5-hexylpyridine,
2-[p-(3-butenyloxy)phenyl]-5-hexylpyridine, m.p. (C—I) 43.5° C., phase transition (S—I), 42.7° C.,
2-[p-(4-pentenyloxy)phenyl]-5-pentylpyridine,
2-[p-(4-pentenyloxy)phenyl]-5-hexylpyridine,
5-[p-(allyloxy)phenyl]-2-hexylpyridine,
5-[p-(2E-butenyloxy)phenyl]-2-hexylpyridine,
5-[p-(3-butenyloxy)phenyl]-2-hexylpyridine.

EXAMPLE 4

142 mg of (S)-2-fluorocaproic acid and 300 mg of p-(5-octyl-2-pyridyl)phenol were dissolved in 10 ml of methylene chloride. The solution was treated with 50 mg of 4-(di-methylamino)pyridine and 258 mg of dicyclohexylcarbodiimide and stirred under nitrogen for 24 hours. The reaction mixture was then filtered and the residue was washed with methylene chloride. The organic phase was evaporated and the residue was purified by chromatography on silica gel with ethyl acetate/hexane (vol. 1:19). Subsequent crystallization from hexane gave 306 mg (72%) of (S)-2-fluorocaproyl p-(5-octyl-2-pyridyl)phenolate with m.p. 69.8° C. and a monotropic smectic phase.

The following compounds can be manufactured in an analogous manner:
(S)-2-Fluorocaproyl p-(5-nonyl-2-pyridyl)phenolate,
(S)-2-fluorocaproyl p-(5-decyl-2-pyridyl)phenolate,
(S)-2-fluorocaproyl trans-4-[p-(5-butyl-2-pyridyl)phenyl]cyclohexanolate,
(S)-2-fluorocaproyl trans-4-[p-(5-pentyl-2-pyridyl)phenyl]cyclohexanolate,
(S)-2-fluorocaproyl trans-4-[p-(5-hexyl-2-pyridyl)phenyl]cyclohexanolate,
(S)-2-fluorocaproyl trans-4-[p-(5-heptyl-2-pyridyl)phenyl]cyclohexanolate,
(S)-2-fluorocaproyl trans-4-[p-(5-octyl-2-pyridyl)phenyl]cyclohexanolate,
(S)-2-fluorocaproyl trans-4-[p-(5-nonyl-2-pyridyl)phenyl]cyclohexanolate,
(S)-2-fluorocaproyl trans-4-[p-(5-(4-pentenyl)-2-pyridyl)phenyl]cyclohexanolate,
(S)-2-fluorocaproyl trans-4-[p-(5-(5-hexenyl)-2-pyridyl)phenyl]cyclohexanolate, (S)-2-fluorocaproyl trans-4-[p-(5-(3E-hexenyl)-2-pyridyl)phenyl]cyclohexanolate.

EXAMPLE 5 p-(5-Heptyl-2-pyridyl)benzoic acid can be converted into (S)-2-octyl p-(5-heptyl-2-pyridyl)benzoate with (S)-2- -octanol according to the method described in Example 4.

The following compounds can be manufactured in an analogous manner:
(S)-2-Octyl p-(5-pentyl-2-pyridyl)benzoate,
(S)-2-octyl p-(5-hexyl-2-pyridyl)benzoate,
(S)-6-methyloctyl p-(5-pentyl-2-pyridyl)benzoate,
(S)-6-methyloctyl p-(5-hexyl-2-pyridyl)benzoate,
(S)-6-methyloctyl p-(5-heptyl-2-pyridyl)benzoate,
(S)-2-chlorononyl p-(5-pentyl-2-pyridyl)benzoate,
(S)-2-chlorononyl p-(5-hexyl-2-pyridyl)benzoate,
(S)-2-chlorononyl p-(5-heptyl-2-pyridyl)benzoate.

EXAMPLE 6

A suspension of 6.64 g of methyltriphenylphosphonium bromide in 80 ml of t-butyl methyl ether in a sulphonation flask fitted with a mechanical stirrer is treated while gassing with argon at −10° C. within 3 minutes with 2.12 g of solid potassium t-butylate. The mixture is stirred at room temperature for a further 1 hour, then treated at 0° C. within 5 minutes with a solution of 3.61 g of 4-[2-(p-bromophenyl)- -5-pyridyl]-butyraldehyde in 20 ml of t-butyl methyl ether and stirred at room temperature for a further 15 hours. The reaction mixture is subsequently partitioned three times in diethyl ether/water. The organic extracts are washed twice with water, dried over magnesium sulphate, filtered and evaporated. The residue is taken up in ethyl acetate and then the mixture is diluted with petroleum ether and filtered. Evaporation of the filtrate and purification of the residue by chromatography on silica gel gives 2-(p-bromophenyl)-5-(4-pentenyl)pyridine.

The following compounds can be manufactured in an analogous manner;
2-(p-Bromophenyl)-5-(3-butenyl)pyridine,
2-(p-bromophenyl)-5-(3E-pentenyl)pyridine,
2-(p-bromophenyl)-5-[4-(4-pentenyl)phenyl]pyridine,
2-(p-bromophenyl)-5-[trans-4-(4-pentenyl)cyclohexyl]-pyridine,
2-(p-butylphenyl)-5-(4-pentenyl)pyridine,
2-(p-butylphenyl)-5-(3E-pentenyl(pyridine,
2-(p-pentylphenyl)-5-(4-pentenyl)pyridine,
5-butyl-2-[p-(4-pentenyl)phenyl]pyridine,
5-butyl-2-[p-(3E-pentenyl)phenyl]pyridine,
5-pentyl-2-[p-(4-pentenyl)phenyl]pyridine,
2-(trans-4-propylcyclohexyl)-5-(4-pentenyl)pyridine,
2-(trans-4-propylcyclohexyl)-5-(3E-pentenyl)pyridine,
2-(trans-4-butylcyclohexyl)-5-(4-pentenyl)pyridine,
2-(trans-4-butylcyclohexyl)-5-(3E-pentenyl)pyridine,
2-(trans-4-pentylcyclohexyl-5-(4-pentenyl)pyridine,
2-(trans-4-pentylcyclohexyl-5-(3E-pentenyl)pyridine,
2-(trans-4-heptylcyclohexyl-5-(4-pentenyl)pyridine,
2-(trans-4-heptylcyclohexyl-5-(3E-pentenyl)pyridine.

EXAMPLE 7

(a) A solution of 0.7 g of hydroxylamine hydrochloride in 1.58 g of pyridine is treated with 3.41 g of 5-hexyl-2-[p-(trans-4-formylcyclohexyl)phenyl]pyridine and stirred at room temperature for 5 minutes. The reaction mixture is then treated with 20 ml of toluene and heated to reflux for 4 hours under water separation. The cooled reaction mixture is filtered. The filtrate is diluted with diethyl ether, washed several times with water and dried over magnesium sulphate. After evaporation there is obtained 5-hexyl-2-[p- -(4-cyanocyclohexyl)-phenyl]pyridine as a cis/trans mixture.

(b) 105 ml of tetrahydrofuran are cooled to −74° C. in a sulphonation flask while gassing with argon and treated dropwise in succession with 1.81 ml of diisopropylamine and 7.8 ml of a 1.6M solution of butyllithium in hexane. The mixture is stirred for a further 15 minutes and then left to warm to −50° C. The mixture is subsequently treated dropwise with a solution of 3.7 g of 5-hexyl-2-[p-(4-cyanocyclo-hexyl)phenyl]pyridine in 9.5 ml of tetrahydrofuran and stirred for a further 15 minutes. Thereafter, the reaction mixture is treated dropwise with a solution of 1.62 g of (S)-2-methyl-1-butyl bromide in 9.5 ml of tetrahydrofuran and stirred at −50° C. for 1.5 hours and then at room temper-ature for 1.5 hours. The reaction mixture is subsequently poured into saturated ammonium chloride solution and extracted with diethyl ether. The organic phase is dried over magnesium sulphate and evaporated. Separation of the equatorial nitrile by chromatography gives (S)-5-hexyl-2-[p- -(cis-4-cyano-4-(2-methylbutyl)cyclohexyl)-phenyl]pyridine.

The following compounds can be manufactured in an analogous manner:
(S)-5-Hexyl-2-[p-(cis-4-cyano-4-(3-methylpentyl)cyclohexyl)phenyl]pyridine,
(S)-5-hexyl-2-[p-(cis-4-cyano-4-(2-fluorohexyl)cyclohexyl)phenyl]pyridine,
(S)-5-octyl-2-[p-(cis-4-cyano-4-(2-methylbutyl)cyclohexyl)phenyl]pyridine,
(S)-5-octyl-2-[p-(cis-4-cyano-4-(3-methylpentyl)cyclohexyl)phenyl]pyridine,
(S)-5-octyl-2-[p-(cis-4-cyano-4-(2-fluorohexyl)cyclohexyl)phenyl]pyridine,
(S)-5-nonyl-2-[p-(cis-4-cyano-4-(2-methylbutyl)cyclohexyl)phenyl]pyridine,
(S)-5-nonyl-2-[p-(cis-4-cyano-4-(3-methylpentyl)cyclohexyl)phenyl]pyridine,
(S)-5-nonyl-2-[p-(cis-4-cyano-4-(2-fluorohexyl)cyclohexyl)phenyl]pyridine,
(S)-5-(4-pentenyl)-2-[p-(cis-4-cyano-4-(2-methylbutyl)-cyclohexyl)phenyl]pyridine,
(S)-5-(4-pentenyl)-2-[p-(cis-4-cyano-4-(3-methylpentyl)-cyclohexyl)phenyl]pyridine,
(S)-5-(4-pentenyl)-2-[p-(cis-4-cyano-4-(2-fluorohexyl)-cyclohexyl)phenyl]pyridine,
(S)-5-(5-hexenyl)-2-[p-(cis-4-cyano-4-(2-methylbutyl)-cyclohexyl)phenyl]pyridine,
(S)-5-(5-hexenyl)-2-[p-(cis-4-cyano-4-(3-methylpentyl)-cyclohexyl)phenyl]pyridine,
(S)-5-(5-hexenyl)-2-[p-(cis-4-cyano-4-(2-fluorohexyl)-cyclohexyl)phenyl]pyridine.

EXAMPLE 8

(a) A mixture of 0.248 g of 2-(p-bromophenyl)-5-methyl-pyridine, 0.196 g of N-bromosuccinimide, 20 mg of dibenzoyl peroxide and 5 ml of carbon tetrachloride was heated to reflux for 2.5 hours while gassing with nitrogen. The reaction mixture was subsequently left to cool to room temperature and suction filtered. The residue was rinsed with carbon tetrachloride. The filtrate was concentrated in a vacuum, there being obtained 0.360 g of crude 2-(p-bromophenyl)-5-bromomethyl-pyridine as brownish crystals.

(b) A mixture of 0.360 g of crude 2-(p-bromophenyl)-5-bromo-methyl-pyridine, 0.5 ml of pyridine and 4 ml of benzene was boiled at reflux for 1 hour. The yellow suspension was sub-sequently cooled to room temperature and suction filtered. The residue was washed with benzene and dried in a vacuum. There was thus obtained 0.266 g of N-[2-(p-bromophenyl)-5- -pyridyl]-methyl-pyridinium bromide as brownish crystals of m.p. 264°–268.5° C. (decomposition).

(c) A mixture of 0.266 g of N-[2-(p-bromophenyl)-5-pyridyl]-methyl-pyridinium bromide, 0.105 g of 4-nitroso-N,N-di-methylaniline and 2 ml of ethanol was treated with 0.1 ml of 3N sodium hydroxide solution while stirring and stirred at room temperature for a further 1 hour. The reaction mixture was subsequently treated with 2 ml of 3N hydrochloric acid and extracted twice with 50 ml of methylene chloride each time. The methylene chloride phases were washed with 50 ml of water, dried over sodium sulphate and evaporated in a vacuum. The crude product (120 mg of green crystals) was purified by chromatography on silica gel with methylene chloride at 0.4 bar. There were thus obtained 94 mg of 2-(p-bromophenyl)-5-pyridinecarboxaldehyde as yellow crystals; m.p. 108.4°–109.0° C. after recrystallization from methylene chloride/hexane.

The following compounds can be prepared in an analogous manner:
5-(p-Bromophenyl)-2-pyridinecarboxaldehyde,
4-[2-(p-bromophenyl)-5-pyridyl]benzaldehyde,
4-[5-(p-bromophenyl)-2-pyridyl]benzaldehyde,
2-(trans-4-propylcyclohexyl)-5-pyridinecarboxaldehyde,
2-(trans-4-butylcyclohexyl)-5-pyridinecarboxaldehyde,
2-(trans-4-pentylcyclohexyl)-5-pyridinecarboxaldehyde,
2-(trans-4-heptylcyclohexyl)-5-pyridinecarboxaldehyde.

EXAMPLE 9

(a) A solution of 16.3 g of p-[trans-4-(p-anisyloxymethyl)-cyclohexyl]benzoyl chloride in 50 ml of dichloroethane is cooled to 7° C. and treated portionwise under nitrogen within 5 minutes with 6.4 g of powdered aluminium chloride. A weak stream of acetylene gas is then conducted through the reaction mixture at 45° C. for 17 hours. The reaction mixture is subsequently poured into 100 ml of ice-water, treated with 50 ml of 3N hydrochloric acid and stirred for 10 minutes. The mixture is extracted with diethyl ether. The organic phase is washed in succession with water, with 5 percent potassium hydroxide solution and several times with water, then dried over magnesium sulphate and evaporated. The trans-4-(p-anisyloxymethyl)-1-[p-(3-chloroacryloyl)phenyl]cyclohexane obtained is purified by chromatography on silica gel.

(b) A mixture of 3.15 g of N-(1-octenyl)piperidine, 2 ml of triethylamine and 25 ml of diethyl ether is treated dropwise while gassing with nitrogen with a solution of 6 g of trans- -4-(p-anisyloxymethyl)-1-[p-(3-chloroacryloyl)phenyl]cyclo-hexane in 8 ml of diethyl ether. The suspension is stirred at room temperature for 2.5 hours and then partitioned between water and diethyl ether. The organic phase is washed several times with water, dried over magnesium sulphate and evaporated. The residue is added portionwise while cooling to 25 ml of 9 percent aqueous perchloric acid. The mixture is stirred for 15 minutes, then treated with 10 ml of ethanol and stirred for a further 4.5 hours. The resulting precipitate of 5-hexyl-2-[p-(trans-4-(p-anisyloxymethyl)-cyclohexyl)phenyl]pyryllium perchlorate is filtered off, washed with a small amount of ice-cold ethanol and dried in a high vacuum.

(c) A solution of 3.17 g of 5-hexyl-2-[p-(trans-4-(p-anisyloxymethyl)cyclohexyl)phenyl]pyryllium perchlorate and 0.38 g of ammonium acetate in 30 ml of glacial acetic acid is heated to reflux for 30 minutes. Thereafter, the reaction mixture is partitioned between methylene chloride and water. The organic phase is washed in succession with water, with saturated sodium hydrogen carbonate solution and twice with water, dried over magnesium sulphate and evaporated. The 5- -hexyl-2-[p-(trans-4-(p-anisyloxymethyl)cylohexyl)phenyl]-pyridine obtained is purified by chromatography on silica gel.

(d) A mixture of 0.485 g of 5-hexyl-2-[p-(trans-4-(p-anisyloxymethyl)cyclohexyl)phenyl]pyridine, 9.6 ml of acetonitrile and 2.4 ml of water is treated at 0° C. with 1.25 g of cer-(IV) ammonium nitrate. After 10 minutes the reaction mixture is diluted with water and extracted with diethyl ether. The organic phase is washed several times with water, then dried over magnesium sulphate and evaporated. Purification of the residue by chromatography on silica gel gives 5-hexyl-2-[p-(trans-4-(hydroxymethyl)-cyclohexyl)phenyl]pyridine.

(e) A solution of 0.94 ml of oxalyl chloride in 25 ml of dry methylene chloride is treated dropwise at −60° C. within 10 minutes with a solution of 1.56 ml of dimethyl sulphoxide in 5 ml of methylene chloride. 2 minutes later the reaction mixture is treated dropwise at −60° C. within 10 minutes with a solution of 3.51 g of 5-hexyl-2-[p-(trans-4-(hydroxymethyl)cyclohexyl)phenyl]-pyridine in 10 ml of methylene chloride and stirred at −60° C. for a further 15 minutes. Thereafter, the reaction mixture is treated with 7 ml of triethylamine, left to warm to room temperature and then poured into water and extracted with methylene chloride. The organic phase is washed twice with water, dried over magnesium sulphate and evaporated. The 5-hexyl-2-[p-(trans- -4-formylcyclohexyl)phenyl]pyridine obtained is purified by chromatography on silica gel.

The p-[trans-4-(p-anisyloxymethyl)cyclohexyl]benzoyl chloride used as the starting material can be prepared, for example, from p-[trans-4-(hydroxymethyl)-cyclohexyl]benzo-nitrile by etherification with p-hydroxyanisole in an analo-gous manner to Tetr. Letters 26, 6291 (1985), saponification of the nitrile group with potassium hydroxide solution and reaction of the carboxylic acid with thionyl chloride to give the carboxylic acid chloride.

The following compounds can be prepared in an analogous manner:
5-Octyl-2-[p-(trans-4-formylcyclohexyl)phenyl]pyridine,
5-nonyl-2-[p-(trans-4-formylcyclohexyl)phenyl]pyridine,
5-bromo-2-[p-(trans-4-formylcyclohexyl)phenyl]pyridine,
5-bromo-2-[p-(trans-4-formylcyclohexyl)phenyl]pyridine.

EXAMPLE 10

(a) A suspension of 29.0 g of methoxymethyl-triphenylphosphonium chloride in 200 ml of t-butyl methyl ether in a sulphonation flask fitted with a mechanical stirrer is treated while gassing with argon at −10° C. within 3 minutes with 9.7 g of potassium t-butylate. The orange suspension is stirred at about 0° C. for a further 1 hour, then treated dropwise at −10° C.

within 10 minutes with a solution of 14.76 g of 2-(p-bromophenyl)-5-pyridinecarboxaldehyde in 90 ml of t-butyl methyl ether and stirred at 0° C. for a further 45 minutes. The reaction mixture is subsequently partitioned three times in diethyl ether/water. The organic extracts are washed twice with water, dried over magnesium sulphate, filtered and evaporated. In order to separate triphenylphosphine oxide, the residue is dissolved in ethyl acetate and the solution is diluted with petroleum ether, filtered and evaporated. Purification of the residue by chromatography on silica gel gives 2-(p-bromophenyl)-5-(2-methoxyvinyl)pyridine.

(b) A solution of 12.4 g of 2-(p-bromophenyl)-5-(2-methoxyvinyl)pyridine in 200 ml of tetrahydrofuran/2N hydrochloric acid (vol. 4:1) is heated to reflux for 1 hour while stirring. The reaction mixture is subsequently partitioned three times in diethyl ether/water. The organic extracts are washed twice with water, dried over magnesium sulphate, filtered and evaporated, whereby [2-(p-bromophenyl)-5-pyridyl]acetaldehyde is obtained as the residue.

(c) [2-(p-Bromophenyl)-5-pyridyl]acetaldehyde is converted in an analogous manner to paragraph (a) into 2-(p-bromophenyl)-5-(3-methoxy-2-propenyl)pyridine and this is then hydrolyzed in an analogous manner to paragraph (b) to give 3-[2-(p-bromophenyl)-5-pyridyl]propionaldehyde.

(d) 3-[2-(p-Bromophenyl)-5-pyridyl]propionaldehyde is converted in an analogous manner to paragraph (a) into 2-(p-bromophenyl)-5-(4-methoxy-3-butenyl)pyridine and this is then hydrolyzed in an analogous manner to paragraph (b) to give 4-[2-(p-bromophenyl)-5-pyridyl]butyraldehyde.

The following compounds can be prepared in an analogous manner:
[5-(p-Bromophenyl)-2-pyridyl]acetaldehyde,
3-[5-(p-bromophenyl)-2-pyridyl]propionaldehyde,
4-[5-(p-bromophenyl)-2-pyridyl]butyraldehyde,
[4-(2-(p-bromophenyl)-5-pyridyl)phenyl]acetaldehyde,
3-[4-(2-(p-bromophenyl)-5-pyridyl)phenyl]propionaldehyde,
4-[4-(2-(p-bromophenyl)-5-pyridyl)phenyl]butyraldehyde,
[4-(5-(p-bromophenyl)-2-pyridyl)phenyl]acetaldehyde,
3-[4-(5-(p-bromophenyl)-2-pyridyl)phenyl]propionaldehyde,
4-[4-(5-(p-bromophenyl)-2-pyridyl)phenyl]butyraldehyde,
[trans-4-(2-(p-bromophenyl)-5-pyridyl)cyclohexyl]acetaldehyde,
3-[trans-4-(2-(p-bromophenyl)-5-pyridyl)cyclohexyl]propionaldehyde,
4-[trans-4-(2-(p-bromophenyl)-5-pyridyl)cyclohexyl]butyralaldehyde,
[2-(p-butylphenyl)-5-pyridyl]acetaldehyde,
3-[2-(p-butylphenyl)-5-pyridyl]propionaldehyde,
4-[2-(p-butylphenyl)-5-pyridyl]butyraldehyde,
[p-(5-butyl-2-pyridyl)phenyl]acetaldehyde,
3-[p-(5-butyl-2-pyridyl)phenyl]propionaldehyde,
4-[p-(5-butyl-2-pyridyl)phenyl]butyraldehyde,
[trans-4-(p-(5-Hexyl-2-pyridyl)phenyl)cyclohexyl]acetaldehyde,
3-[trans-4-(p-(5-hexyl-2-pyridyl)phenyl)cyclohexyl]propionaldehyde,
4-[trans-4-(p-(5-hexyl-2-pyridyl)phenyl)cyclohexyl]butyraldehyde,
[trans-4-(p-(5-octyl-2-pyridyl)phenyl)cyclohexyl]acetaldehyde,
3-[trans-4-(p-(5-octyl-2-pyridyl)phenyl)cyclohexyl]propionaldehyde,
4-[trans-4-(p-(5-octyl-2-pyridyl)phenyl)cyclohexyl]butyraldehyde,
[trans-4-[p-(5-(4-pentenyl)-2-pyridyl)phenyl)cyclohexyl]acetaldehyde,
3-[trans-4-[p-(5-(4-pentenyl)-2-pyridyl)phenyl]cyclohexyl]propionaldehyde,
4-[trans-4-[p-(5-(4-pentenyl)-2-pyridyl)phenyl]cyclohexyl]butyraldehyde,
[2-(trans-4-propylcyclohexyl)-5-pyridyl]acetaldehyde,
3-[2-(trans-4-propylcyclohexyl)-5-pyridyl]propionaldehyde,
4-[2-(trans-4-propylcyclohexyl)-5-pyridyl]butyraldehyde,
[2-(trans-4-butylcyclohexyl)-5-pyridyl]acetaldehyde,
3-[2-(trans-4-butylcyclohexyl)-5-pyridyl]propionaldehyde,
4-[2-(trans-4-butylcyclohexyl)-5-pyridyl]butyraldehyde,
[2-(trans-4-pentylcyclohexyl)-5-pyridyl]acetaldehyde,
3-[2-(trans-4-pentylcyclohexyl)-5-pyridyl]propionaldehyde,
4-[2-(trans-4-pentylcyclohexyl)-5-pyridyl]butyraldehyde,
[2-(trans-4-heptylcyclohexyl)-5-pyridyl]acetaldehyde,
3-[2-(trans-4-heptylcyclohexyl)-5-pyridyl]propionaldehyde,
4-[2-(trans-4-heptylcyclohexyl)-5-pyridyl]butyraldehyde.

The corresponding valeraldehydes, capronaldehydes, heptaldehydes etc can be obtained by further chain-lengthening reactions.

EXAMPLE 11 p-[trans-4-(p-Anisyloxy)cyclohexyl]benzoyl chloride is converted into 5-octyl-2-[p-trans-4-hydroxycyclohexyl]-phenyl]pyridine according to the methods described in Example 9, steps (a) to (d).

The following compounds can be prepared in an analogous manner:
5-Butyl-2-[p-(trans-4-hydroxycyclohexyl)phenyl]pyridine,
5-pentyl-2-[p-(trans-4-hydroxycyclohexyl)phenyl]pyridine,
5-hexyl-2-[p-(trans-4-hydroxycyclohexyl)phenyl]pyridine,
5-heptyl-2-[p-(trans-4-hydroxycyclohexyl)phenyl]pyridine,
5-nonyl-2-[p-(trans-4-hydroxycyclohexyl)phenyl]pyridine.
5-(4-pentenyl)-2-[p-(trans-4-hydroxycyclohexyl)phenyl]-pyridine,
5-(5-hexenyl)-2-[p-(trans-4-hydroxycyclohexyl)phenyl]-pyridine,
5-(7-octenyl)-2-[p-(trans-4-hydroxycyclohexyl)phenyl]-pyridine.

EXAMPLE 12

(a) A solution of 12.2 g of trans-4-heptylcyclohexanecarboxylic acid chloride in 50 ml of carbon tetrachloride is cooled to 0° C. while stirring and treated portionwise within 10 minutes with 7 g of powdered aluminium chloride. Thereafter, acetylene gas is conducted into the reaction mixture at 0°-3° C. for 8 hours. The reaction mixture is subsequently poured on to ice and 60 ml of 3N hydrochloric acid. The mixture is stirred for 30 minutes and then extracted three times with diethyl ether. The organic phases are washed in succession with water, with 5% potassium hydroxide solution and three times with water, then dried over sodium sulphate and concentrated. There is thus obtained trans-4-heptyl-1-(3-chloroacryloyl)cyclohexane (11.6 g) as a brownish liquid.

(b) A mixture of 6 g of N-(1-propenyl)piperidine, 45 ml of of diethyl ether and 4.36 ml of triethylamine is treated dropwise while stirring and gassing with nitrogen at 0° C. within 1 hour with a solution of 8.5 g of trans-4-heptyl-1-(3-chloroacryloyl)cyclohexane in 20 ml of diethyl ether. The suspension is stirred at 0° C. for a further 1 hour and then treated with 120 ml of water and extracted three times with diethyl ether. The organic phases are washed twice with water, dried over sodium sulphate, filtered and concentrated, there being obtained N-[5-(trans-4-heptylcyclohexyl)-2-methyl-5-oxo-1,3-pentadienyl]piperidine.

(c) A mixture of 25 ml of 70 percent perchloric acid, 25 ml of water and 25 ml of ethanol is cooled to room temperature, then treated with 8.7 g of the obtained N-[5-(trans-4-heptylcyclohexyl)-2-methyl-5-oxo-1,3-pentadienyl]piperidine and stirred at room temperature for a further 1.75 hours. The reaction mixture is subsequently treated with 160 ml of water and extracted three times with methylene chloride. The organic phases are washed twice with water, dried over sodium sulphate and concentrated. There is thus obtained 2-(trans-4-heptylcyclohexyl)-5-methylpyryllium perchlorate.

(d) A mixture of 8.3 g of 2-(trans-4-heptylcyclohexyl)-5-methylpyryllium perchlorate, 116 ml of glacial acetic acid and 3.57 g of ammonium acetate is heated to reflux for 30 minutes. Thereafter, the reaction mixture is cooled to room temperature, treated with 180 ml of water and extracted twice with methylene chloride. The organic phases are washed in succession with water, with 10 percent aqueous sodium carbonate solution and twice with water, then dried over sodium sulphate and filtered. Concentration of the filtrate and purification of the residue by chromatography give 2-(trans-4-heptylcyclohexyl)-5-methylpyridine.

The following compounds can be prepared in an analogous manner:

2-(trans-4-Propylcyclohexyl)-5-methylpyridine,
2-(trans-4-butylcyclohexyl)-5-methylpyridine,
2-(trans-4-pentylcyclohexyl)-5-methylpyridine,
(S)-2-(trans-4-(3-methyloctyl)cyclohexyl)-5-heptylpyridine,
(S)-2-(trans-4-(3-methyloctyl)cyclohexyl)-5-nonylpyridine,
(S)-2-(trans-4-(7-methylnonyl)cyclohexyl)-5-heptylpyridine,
(S)-2-(trans-4-heptylcyclohexyl)-5-(1-methyloctyl)pyridine,
(S)-2-(trans-4-heptylcyclohexyl)-5-(3-methyloctyl)pyridine,
(S)-2-(trans-4-pentylcyclohexyl)-5-(2-methylbutyl)pyridine.

EXAMPLE 13

(nematic mixture)

14 wt.% of p-(trans-4-propylcyclohexyl)benzonitrile,
19 wt.% p-[trans-4-(4-pentenyl)cyclohexyl]benzonitrile,
11 wt.% 4'-[trans-4-(4-pentenyl)cyclohexyl]-4-biphenylcarbonitrile,
14 wt.% p-(5-butyl-2-pyrimidinyl)benzonitrile,
4 wt.% p-(5-pentyl-2-pyrimidinyl)benzonitrile,
6 wt.% p-[5-(trans-4-ethylcyclohexyl)-2-pyrimidinyl]benzonitrile,
10 wt.% p-[trans-5-(4-pentenyl)-m-dioxan-2-yl]phenylisothiocyanate,
7 wt.% p-(4-pentenyl)benzoic acid 4-cyano-3-fluorophenyl ester,
7 wt.% trans-4-propylcyclohexanecarboxylic acid-p-[trans-4-(3E-pentenyl)cyclohexylphenyl ester,
8 wt.% p-(5-pentyl-2-pyridyl)phenylisothiocyanate;
m.p. (C—N) < −20° C., cl.p. (N—I) 61° C.; $p_o$=0.137, $\Delta n$=0.165.

EXAMPLE 14

(ferroelectric mixtures)

Mixtures A-C were made using the following components:

(S)-p-Nonylbenzoic acid p'-(2-methylbutyloxy)phenyl ester, (C—$S_c^*$) 40.5° C., ($S_c^*$—$S_A$) 47° C., ($S_A$—I) 60° C.;

(S)-5-(5-methylheptyl)-2-(p-octyloxyphenyl)pyrimidine, (C—$S_c^*$) 36.5° C., ($S_c^*$—Ch) 38.5° C., (Ch-I) 51° C.;

(S)-2-[p-(6-methyloctyloxy)phenyl]-5-octylpyridine, (C—S) 36.1° C., (S—$S_c^*$) 57° C., ($S_c^*$—I) 70.4° C.

Mixture A:

75 wt.% of (S)-p-nonylbenzoic acid p'-(2-methylbutyloxy)-phenyl ester,
25 wt.% of (S)-2-[p-(6-methyloctyloxy)phenyl]-5-octylpyridine; (C—$S_c^*$) about 36° C., (S—$S_c^*$) 15° C., ($S_c^*$—$S_A$) 50° C., ($S_A$—I) 60.3° C.

Mixture B:

50 wt.% of (S)-5-(5-methylheptyl)-2-(p-octyloxyphenyl)-pyrimidine,
50 wt.% of (S)-2-[p-(6-methyloctyloxy)phenyl]-5-octylpyridine; ($S_c^*$—I) 56.4° C. The mixture remains chiral smectic C upon cooling to −11° C.

Mixture C:

20 wt.% of (S)-p-nonylbenzoic acid p'-(2-methylbutyloxy)-phenyl ester,
40 wt.% of (S)-5-(5-methylheptyl)-2-(p-octyloxyphenyl)pyrimidine,
40 wt.% of (S)-2-[p-(6-methyloctyloxy)phenyl]-5-octylpyridine; ($S_c^*$—Ch) 51.6° C., (Ch—I) 52.7° C. The chiral smectic C phase can be observed upon cooling to below −23° C.

We claim:

1. A compound of the formula:

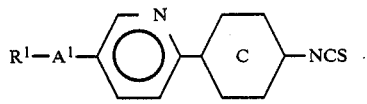

Ia wherein $R^1$ is alkyl, alkoxy, alkenyl or alkenyloxy; $A^1$ is a single covalent bond, trans-1,4-cyclohexylene or 1,4-phenylene; and ring C is 1,4-phenylene.

2. The compound of claim 1, wherein $R^1$ and $R^2$ each have a maximum of 18 carbon atoms.

3. The compound of claim 1, wherein $R^1$ is straight-chain alkyl, alkoxy, alkenyl or alkenyloxy with 1 to 12 carbon atoms.

4. The compound of claims 1, wherein $R^1$ is straight-chain alkyl, alkoxy, alkenyl or alkenyloxy with 1 to 7 carbon atoms, $A^1$ is a single covalent bond and ring C is 1,4-phenylene.

5. The compound according to claim 1, wherein $R^1$ is alkyl, alkoxy, 1E-alkenyl, 3E-alkenyl, 4-alkenyl, 2E-alkenyloxy or 3-alkenyloxy.

6. The compound of claim 1, p-(5-pentyl-2-pyridyl)-phenylisothiocyanate.

7. The compound of claim 1, p-(5-hexyl-2-pyridyl)-phenylisothiocyanate.

8. A liquid crystalline mixture comprising at least two components, wherein at least one of the components is a compound of the formula

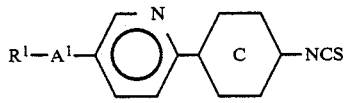
Ia wherein $R^1$ is alkyl, alkoxy, alkenyl or alkenyloxy; $A^1$ is a single covalent bond, trans-1,4-cyclohexylene or 1,4-phenylene; and ring C is 1,4-phenylene.

9. An electro-optical cell comprising:
(a) two plate means;
(b) liquid crystal means disposed between the two plate means and including a compound of the formula

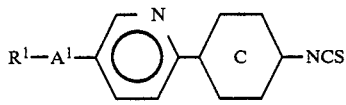
Ia wherein $R^1$ is alkyl, alkoxy, alkenyl or alkenyloxy; $A^1$ is a single covalent bond, trans-1,4-cyclohexylene or 1,4-phenylene; and ring C is 1,4-phenylene; and
(c) means for applying electric potential to said plate means.

* * * * *